(12) United States Patent
Jaracz et al.

(10) Patent No.: US 11,517,512 B2
(45) Date of Patent: Dec. 6, 2022

(54) PERSONAL CARE COMPOSITIONS COMPRISING ZINC : USNIC ACID COMPLEXES AND METHODS OF USE

(71) Applicant: Colgate-Palmolive Company, New York, NY (US)

(72) Inventors: Stanislav Jaracz, Somerset, NJ (US); Long Pan, Somerset, NJ (US); Karthik Sambanthamoorthy, Bridgewater, NJ (US); Junhong Mao, Plainsboro, NJ (US); Aixing Fan, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 220 days.

(21) Appl. No.: 16/631,481

(22) PCT Filed: Jul. 16, 2018

(86) PCT No.: PCT/US2018/042287
§ 371 (c)(1),
(2) Date: Jan. 16, 2020

(87) PCT Pub. No.: WO2019/018287
PCT Pub. Date: Jan. 24, 2019

(65) Prior Publication Data
US 2021/0401694 A1   Dec. 30, 2021

Related U.S. Application Data

(60) Provisional application No. 62/534,420, filed on Jul. 19, 2017.

(51) Int. Cl.
*A61K 8/27* (2006.01)
*A61K 8/49* (2006.01)
*A61Q 17/00* (2006.01)
*A61Q 19/10* (2006.01)
*A61K 8/44* (2006.01)
*A61K 8/42* (2006.01)

(52) U.S. Cl.
CPC .............. *A61K 8/27* (2013.01); *A61K 8/42* (2013.01); *A61K 8/44* (2013.01); *A61K 8/4973* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 5,362,482 A * | 11/1994 | Yoneyama | A61K 8/06 424/403 |
| 6,927,201 B2 | 8/2005 | Hsu et al. | |
| 9,855,200 B2 | 1/2018 | Campbell | |
| 2008/0233145 A1 * | 9/2008 | Schempp | A61K 9/0014 424/195.15 |
| 2012/0270935 A1 | 10/2012 | Davis et al. | |
| 2014/0057976 A1 * | 2/2014 | Abbott | A61K 47/22 514/468 |

FOREIGN PATENT DOCUMENTS

| | | |
|---|---|---|
| CN | 104231255 | 12/2014 |
| CN | 105030620 A * | 11/2015 |
| CN | 105411871 | 3/2016 |
| CN | 105616285 | 6/2016 |
| CN | 106420562 | 2/2017 |
| EP | 0256566 | 2/1988 |
| GB | 1010200 | 11/1965 |
| GB | 2481512 | 12/2011 |
| RU | 2481098 | 5/2013 |
| WO | 1999/030680 | 6/1999 |
| WO | 2008/017296 | 2/2008 |
| WO | 2016/144907 | 9/2016 |
| WO | 2019/018287 | 1/2019 |

OTHER PUBLICATIONS

Zinc Sulfate Heptahydrate Product Information Sheet (Year: 2003).*
Basile et al., 2015, "Antiproliferative, antibacterial and antifungal activity of the lichen *Xanthoria parietina* and its secondary metabolite parietin," Int. J. Mol. Sci. 16(4):7861-7875.
Gao et al., 2014, "Preparing complex compound used for preparing dandruff and hair washing liquid for preventing *Staphylococcus aureus*, *Escherichia coli* and fungi infection, involves utilizing fatty alcohol polyethenoxy ether, usnic acid and citric acid," WPI Database AN: 2015-11358E.
Hauck et al., 2009, "Dissociation and metal-binding characteristics of yellow lichen substances suggest a relationship with site preferences of lichens," Ann. Bot. 103(1):13-22.
Hohenberg et al., 1964, "Inhomogeneous electron gas," Physical Review 136(3B):B864-B871.
International Search Report and Written Opinion of the International Searching Authority in International Application No. PCT/US2018/042287, dated Sep. 26, 2018.
Jin et al., 2013, "Solubility of (+)-Usnic Acid in Water, Ethanol, Acetone, Ethyl Acetate and n-Hexane," J. Solution Chem. 42:1018-1027.
Jing et al., 2016, "Compound medicinal toothpaste comprises friction agent, humectant and deionized water as main ingredient, and tranexamic acid, zinc organic acid, usnic acid or its salt," WPI Database AN: 2016-210930.

(Continued)

*Primary Examiner* — Robert A Wax
*Assistant Examiner* — Caralynne E Helm

(57) ABSTRACT

Disclosed herein are personal care compositions comprising Zn:usnate complexes having a 1:2 zinc to usnate molar ratio. Methods of making and using the compositions are also provided. The personal care compositions may include a cleansing component and an antibacterial component, wherein the antibacterial component comprises Zn:usnate complexes having a 1:2 zinc to usnate molar ratio.

18 Claims, 4 Drawing Sheets

(56) References Cited

OTHER PUBLICATIONS

Shrestha et al., 2013, "Lichens: a promising source of antibiotic and anticancer drugs," Phytochem. Rev. 12(1):229-244.
Takani et al., 2002, "Spectroscopic and structural characterization of copper(II) and palladium(II) complexes of a lichen substance usnic acid and its derivatives. Possible forms of environmental metals retained in lichens," J. Inorg. Biochem. 91(1):139-150.
Zhang, 2016, "Sterilized skin-hand sanitizer contains lauryl amidopropyl amine oxide, chondroitin sulfate, medical stone powder, deionized water, sodium cocoyl glycine, eugenol, usnic acid, sodium lactate, and sodium chloride," WPI Database AN: 2016-370423.
International Search Report and Written Opinion of the International Searching Authority in International Application Mo. PCT/US2018/042790, dated Sep. 26, 2018.
Sun, 2017, "Complex medicinal toothpaste useful for relieving gingival swelling, mouth ulcers and plaque, comprises tranexamic acid, radix rehmanniae, Aloe juice, organic zinc, Meconopsis extract, substrate, usnic acid, hypericin and gallnut," WPI Database AN: 2017-153613, PN CN106420562.

* cited by examiner

PERSONAL CARE COMPOSITIONS COMPRISING ZINC : USNIC ACID COMPLEXES AND METHODS OF USE

CROSS-REFERENCE TO RELATED APPLICATIONS

This application claims priority to U.S. Provisional Patent Application No. 62/534,420 filed Jul. 19, 2017, which is incorporated herein by reference.

FIELD

This invention relates to personal care compositions comprising zinc:usnate complexes as well as to methods of using and of making these compositions.

BACKGROUND

A variety of human ailments owe their origin to pathogenic microorganisms, which include bacteria, virus and fungi. The presence of such pathogenic microorganisms lead to septicaemia, serious infections of upper and lower respiratory tract, CNS, meningitis, intra-abdominal tissue including peritoneum, genito-urinary tract, skin, and soft tissue, and a variety of other infections like systemic mycosis, candidiasis including infections caused by dermatophytes. During the last 100 years, significant progress has been made to combat the diseases caused by such a large family of microbes with innumerable therapeutic agents of diverse chemical and biological nature that have become available as a short and long term cure. Such antimicrobials include aminoglycosides, penicillins, cephalosporins, macrolides, glycopeptides, fluoroquinolones, tetracycline, first and second line anti-TB drugs, anti-leprosy, anti-virals, polyene, triazole and imidazole anti-fungals, combinations like pyrimidine derivatives and trimethoprim and sulphamethoxizole.

Conventional liquid cleansing compositions may often include antibacterial agents to reduce the transmission or risk of infection. For example, antibacterial agents are often used to disinfect surfaces in hospitals, lavatories, food prep facilities, and offices. In another example, liquid cleansing compositions, such as hand soaps and shower gels, often incorporate antibacterial agents to control the presence and growth of pathogenic microorganisms on skin to thereby reduce the transmission of disease or infection.

Solubility and efficacy of antimicrobial entities plays a significant role in delivery and formulation options. For example, having a water soluble antimicrobial allows for incorporation into an aqueous phase of gels, surfactants and emulsions. Further, incorporation of antibacterial agents in sufficient or effective concentrations to control the pathogenic microorganisms may often produce liquid cleansing compositions having undesirable properties. For example, antibacterial agents are generally irritating to the skin when provided in the relatively high concentrations necessary to control the pathogenic microorganisms. Additionally, the antibacterial agents may often strip moisture from the skin, thereby leaving the skin feeling overly dry or chapped. Therefore, having antimicrobial entities which maintain water solubility while also maintaining high efficacy levels are advantageous.

Current antimicrobial products do not adequately address water solubility and efficacy attributes. Accordingly, there is a need for such antimicrobial entities to treat and/or prevent progression of microorganism induced ailments.

SUMMARY OF THE INVENTION

It has been surprisingly found that complexes of zinc and usnate having one mole of zinc to two moles of usnate may be produced. These complexes show unexpected physical-chemical attributes, such as an increase in solubility while maintaining antibacterial activity. Such activity may be useful for use in personal care compositions.

In one embodiment, the invention is a personal care composition comprising at least one antimicrobial, wherein said at least one antimicrobial comprises a Zn:usnate complex having a 1:2 zinc to usnate molar ratio. In a further embodiment, the Zn:usnate complex has a solubility of about 13.5 ppm in water at room temperature. In certain embodiments, the complex has a minimal inhibitory concentration of about 8 parts per million against $S.\ aureus$.

In certain embodiments, the personal care composition is selected from a rinse off composition and a leave on composition. In certain embodiments, the personal care composition is a rinse off composition selected from a bar soap, a body wash, a shower gel, a shampoo, a conditioner, a liquid hand or other soap, a dish soap and a facial wash. In certain embodiments, the personal care composition is a leave-on composition selected from a lotion, a cream, an underarm product, an antiperspirant stick, a gel, a roll-on, an aerosol and a pump spray. In certain embodiments, the rinse off composition comprises a cleansing component. In further aspects, the cleansing component is a liquid soap or a liquid hand soap. In further aspects, the cleansing component comprises one or more surfactants. In certain embodiments, the cleansing component comprises at least 8.0 wt % of the one or more surfactants, and optionally at least 9.0 wt % of the one or more surfactants. In certain embodiments, the one or more surfactants comprise a betaine surfactant. In certain embodiments, the betaine surfactant is cocoamidopropyl betaine.

In certain embodiments, the personal care composition according to any one of the embodiments further comprises a foam enhancer, wherein the foam enhancer is cocamide monoethanolamide.

In certain embodiments, the personal care composition is a leave-on composition selected from a lotion, a cream, an underarm product, an antiperspirant stick, a gel, a roll-on, an aerosol and a pump spray.

The invention is further a method of treating and/or preventing progression of microorganism induced ailments comprising applying an effective amount of a composition described in any one of the embodiments described herein.

In certain embodiments, the invention is a composition obtained or obtainable by combining the ingredients as set forth in any of the preceding compositions and methods.

DETAILED DESCRIPTION

Figure 1:
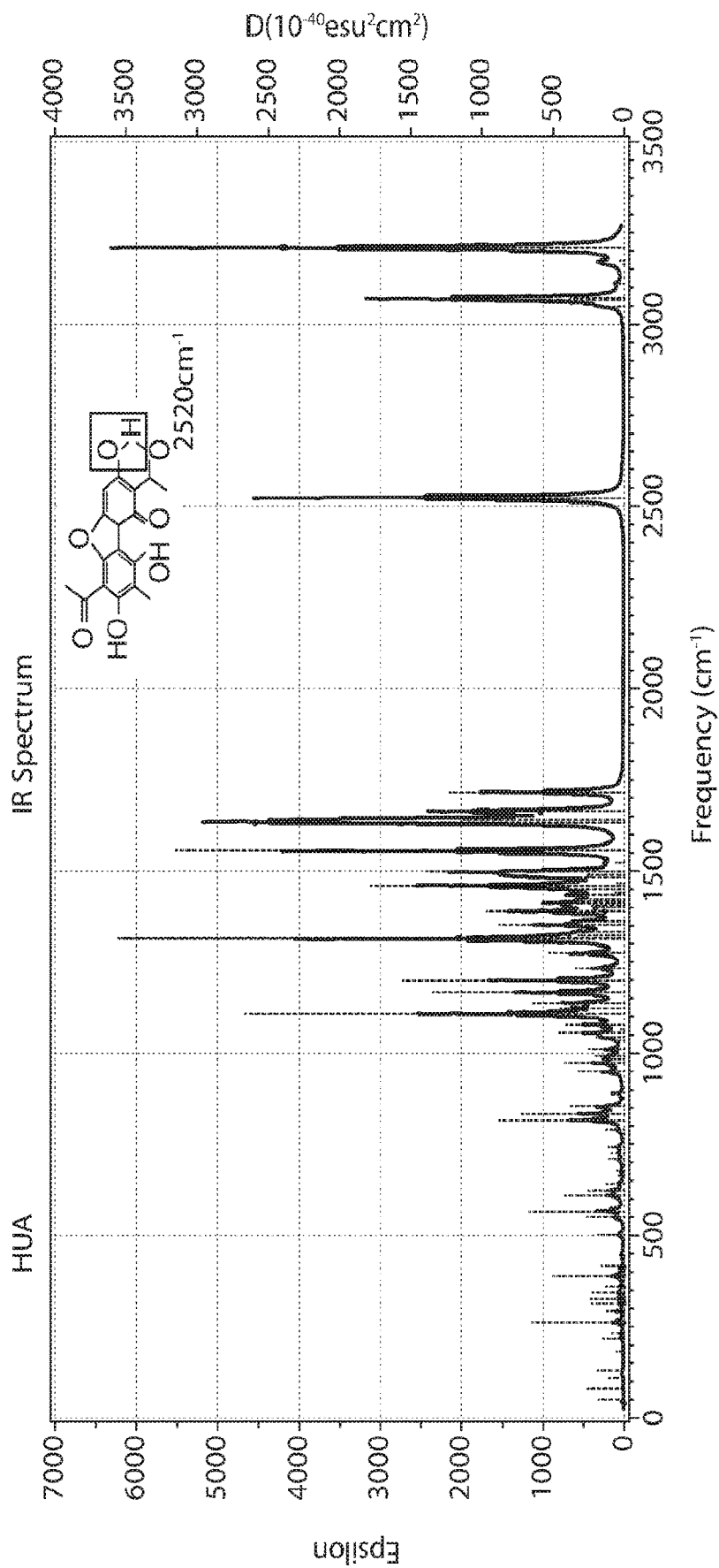
FIG. 1 is a FTIR spectrum of usnic acid.
Figure 2:
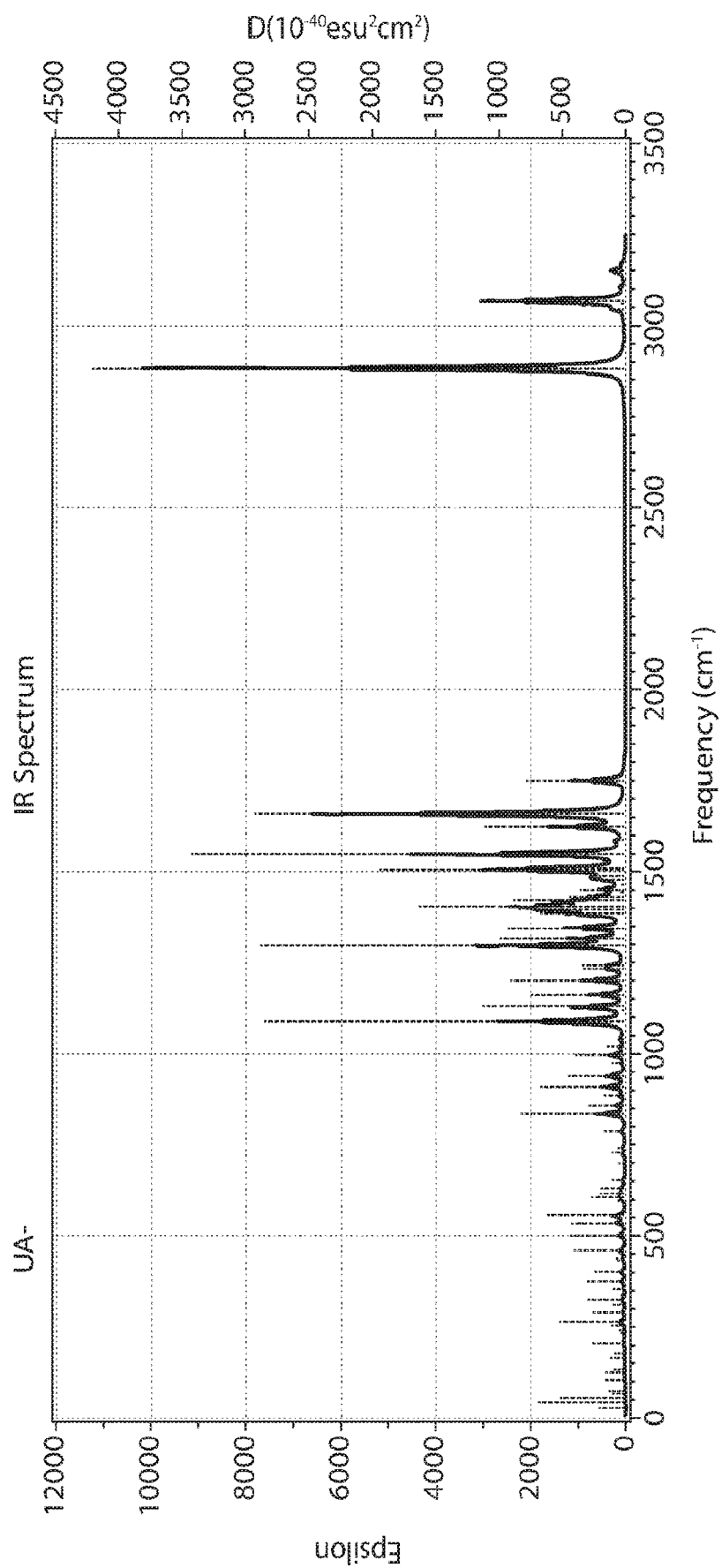
FIG. 2 is a FTIR spectrum of deprotonated usnic acid.
Figure 3:
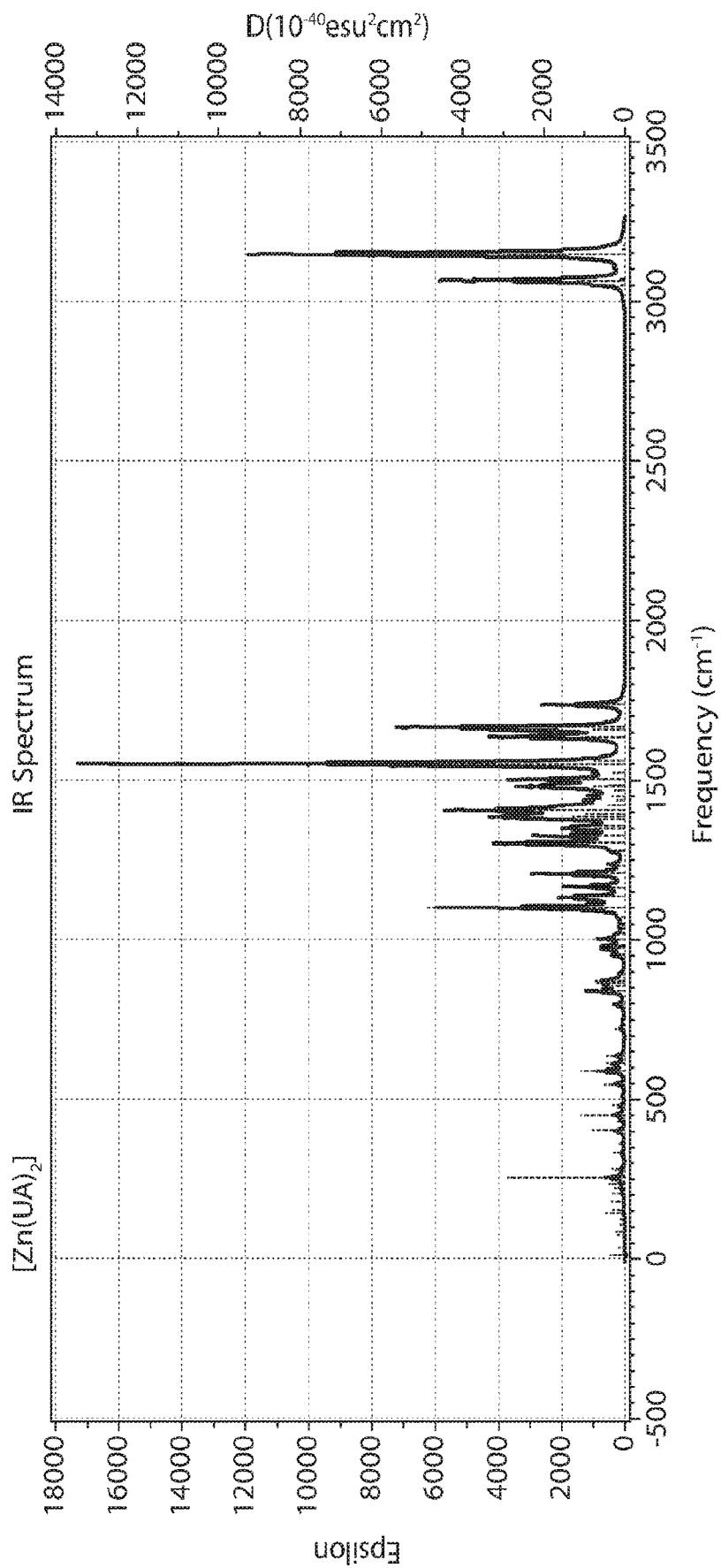
FIG. 3 is a FTIR spectrum of the zinc:usnate complex.

The following description of embodiment(s) of the invention is merely exemplary in nature and is in no way intended to limit the invention, its application, or uses.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range. Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be +/−1% (inclusive) of that numeral, +/−2% (inclusive) of that numeral, +/−3% (inclusive) of that numeral, +/−5% (inclusive) of that numeral, +/−10% (inclusive) of that numeral, or +/−15% (inclusive) of that numeral.

Unless stated otherwise, all percentages of composition components given in this specification are by weight based on a total composition or formulation weight of 100%.

All references cited herein are hereby incorporated by reference in their entireties. In the event of a conflict in a definition in the present disclosure and that of a cited reference, the present disclosure controls.

The term "effective amount" as used herein means that the amount of the composition of the present invention is of sufficient quantity to achieve the intended purpose, such as, for example, to treat and/or prevent progression of microorganism induced ailments.

The terms "1:2 Zn:usnate", "2:1 usnate:Zn complex", "zinc:usnate", "Zn:usnate complex" and "zinc:usnate complex" are used interchangeably and refer, unless specified otherwise, to the complex of the invention.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes, for example, excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

The invention provides for compositions comprising Zn:usnate complex(es), wherein the Zn:usnate complex has a 1:2 zinc to usnate molar ratio. Such complexes provide unique features, such as enhanced antimicrobial activities, useful in personal care applications. In certain embodiments, the zinc:usnate complex is present at 7-10 ppm of the final personal care product. In certain embodiments, the complex is present at 7-100 ppm of the final personal care product. In certain embodiments, the complex is present at 7-500 ppm of the final personal care product. In certain embodiments, the complex is present at 7-1000 ppm of the final personal care product.

The invention further provides for methods of preparing a Zn:usnate complex having a 1:2 zinc to usnate molar ratio. In certain preferred embodiments, the zinc and usnic acid source are combined in an alcohol solution. In certain embodiments, the zinc and usnic acid source are combined in methanol, ethanol, isopropanol, butanol, or the like.

In certain embodiments, the complex is synthesized at a temperature between 20° C. to 80° C. In certain embodiments, the complex is synthesized at a temperature between 25° C. to 75° C. In certain embodiments, the complex is synthesized at a temperature between 30° C. to 70° C. In certain embodiments, the complex is synthesized at a temperature between 35° C. to 65° C. In certain embodiments, the complex is synthesized at a temperature between 20° C. to 40° C. In certain embodiments, the complex is synthesized at a temperature between 40° C. to 60° C. In certain embodiments, the complex is synthesized at a temperature between 60° C. to 80° C. In certain embodiments, the complex is synthesized at a temperature between 20° C. to 25° C.

In certain embodiments, the complex is synthesized at a temperature between 20° C. to 80° C. and in an alcohol solution. In certain embodiments, the complex is synthesized at a temperature between 25° C. to 75° C. and in an alcohol solution. In certain embodiments, the complex is synthesized at a temperature between 30° C. to 70° C. and in an alcohol solution. In certain embodiments, the complex is synthesized at a temperature between 25° C. to 75° C. and in an alcohol solution selected from methanol, ethanol, isopropanol, butanol, or the like. In certain embodiments, the complex is synthesized at a temperature between 30° C. to 70° C. and in an alcohol solution selected from methanol, ethanol, isopropanol, butanol, or the like.

In certain embodiments, the complex is synthesized using one molar equivalent of zinc oxide to ulsnic acid of 1 to 2.5, or 1:1-2.5 of ZnO to ulsnic acid. In certain embodiments, the molar equivalent of zinc oxide to ulsnic acid is 1:1.5 to 2.5. In certain embodiments, the molar equivalent of zinc oxide to ulsnic acid is 1:2 to 2.5.

In certain embodiments, the complex is prepared using one molar equivalent of an acid to zinc oxide of 1.8 to 4.0, or 1:1.8-4.0 of acid to ZnO. In certain embodiments, the molar equivalent of an acid to zinc oxide is 1:2.0 to 3.0. In certain embodiments, the acid is selected from a carboxylic acid. In certain embodiments, the acid is selected from formic acid, lactic acid, propionic acid, butyric acid and acetic acid. In certain embodiments, the acid is a non-carboxylic acid. In certain embodiments, the acid is selected from hydrochloric acid, sulfuric acid, nitric acid, phosphoric acid, perchloric acid and hydrobromic acid. In certain embodiments, the acid is acetic acid.

In certain embodiments, the invention is a method of preparing the 1:2 zinc:usnate complex. In certain embodiments, the complex is prepared at a temperature between 20-80° C. In certain embodiments, preparation of the complex comprises the steps of: mixing a zinc source and usnic acid; adding ethanol; mixing the solution at about 80° C.; and optionally isolating said complex. In further embodiments, preparation of the complex comprises the steps of: mixing a zinc source and acetic acid in water; optionally sonicating the mixture; in a separate container, mixing NaOH and ethanol; mixing the NaOH and ethanol mixture with usnic acid; mixing the solution of a. with the solution of d.; and optionally isolating said complex. In further embodiments, preparation of the complex comprises the steps of: mixing a Zn source, usnic acid and ethanol; adding acetic acid; and optionally isolating said complex.

The invention further provides the use of a composition comprising the 1:2 zinc:usnate complex to reduce and/or inhibit acid erosion of the enamel, reducing or inhibiting gum recession, controlling microbial growth, clean the teeth, reduce bacterially-generated biofilm and plaque, reduce gingivitis, inhibit tooth decay and formation of cavities, and/or reduce dentinal hypersensitivity. The invention further provides for use of a composition comprising the 1:2 zinc:usnate complex for controlling microbial growth. The invention further provides for use of a composition comprising the 1:2 zinc:usnate complex for treating and/or preventing progression of microorganism induced ailments.

The invention further provides a method of making an personal care composition comprising combining usnic acid or usnate and a zinc source in an liquid medium, optionally isolating the complex thus formed in solid form, and combining the zinc:usnate complex with an personal care composition. In certain embodiments, the personal care composition is a bar soap, a body wash, a shower gel, a shampoo, a conditioner, a liquid hand or other soap, a dish soap and a facial wash, a lotion, a cream, an underarm product, an antiperspirant stick, a gel, a roll-on, an aerosol or a pump spray.

"Actives," means compounds that, when applied to a target tissue, provide a benefit or improvement to the target tissue. The actives can be delivered in the form of any personal care formulations, for example a soap, wash, lotion or any other known in the art.

The zinc ion source for complex synthesis may be from any source that provides $Zn^{2+}$ ions efficiently, for example zinc oxide, zinc acetate, zinc chloride, zinc lactate, tetrabasic zinc chloride, zinc carbonate, zinc nitrate, zinc citrate, zinc bis lysinate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2.H_2O$, also referred to as basic zinc chloride, zinc hydroxychloride, or zinc oxychloride. It is a colorless crystalline solid insoluble in water. Both of these materials may be solubilized in water in the presence of usnic acid or usnate and heat, thus providing a source of zinc ions. In certain preferred embodiments, the Zn source is selected from zinc acetate, zinc oxide, zinc chloride, zinc lactate, zinc citrate, or zinc nitrate.

In certain embodiments, the amount of zinc in the composition is 0.005 to 30% by weight of the composition. In certain embodiments, precursors, e.g., zinc sources and usnic acid, are present in amounts such that when combined into the zinc:usnate complex, the complex would be present in an amount of 0.005 to 10% by weight of the composition. In either of these embodiments, the amount of the 1:2 zinc:usnate complex can be varied for the desired purpose, such as a dentifrice or a mouthwash. In other embodiments, the amount of the 1:2 zinc:usnate complex is at least 0.1, at least 0.2, at least 0.3, at least 0.4, at least 0.5, at least 1, at least 2, at least 3, or at least 4 up to 10% by weight of the composition. In other embodiments, the amount of the 1:2 zinc:usnate complex is less than 9, less than 8, less than 7, less than 6, less than 5, less than 4, less than 3, less than 2, less than 1, less than 0.5 to 0.005% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the composition is anhydrous. By anhydrous, there is less than 5% by weight water, optionally less than 4, less than 3, less than 2, less than 1, less than 0.5, less than 0.1 down to 0% by weight water.

In certain embodiments, the invention may make use of one or more antibacterial agents in addition to the zinc:usnate complex. Illustrative antibacterial agents may include, but are not limited to, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl) urea, 1-3-dimethyol-5,5-dimethyl hydantoin, formaldehyde, iodopropynl butyl carbamate, parabens, methylisothiazolinone, mixtures of methylisothiazolinone and methylchloroisothiazoline, mixtures of phenoxyethanol/butyl paraben/methyl paraben/propylparaben, 2-phenoxyethanol, trishydroxyethyl-hexahydrotriaz-ine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, sodium benzoate, polyhexamethylene biguanide, alexidine, triclosan, parachlorometaxylenol, zinc pyrithione, essential oils (e.g., tea tree, eucalyptus, thyme, etc.), silver and salts thereof, chlorhexidine and salts thereof, and the like, and combinations thereof. In a preferred embodiment, the antibacterial agent is phenoxyethanol (i.e., 2-phenoxyethanol).

The liquid cleansing composition may include one or more surfactants. In at least one embodiment, the surfactants may be or include a salt of a $C_{10-16}$ alcohol ethoxylate sulfate, a betaine surfactant, and/or an alkyl polyglucoside. In another embodiment, the liquid cleansing composition may include one or more anionic surfactants, one or more cationic surfactants, one or more zwitterionic surfactants, one or more nonionic surfactants, and mixtures thereof. The amount of the surfactants in the liquid cleansing composition may be from about 5.0 wt % to about 14.0 wt %. For example, the amount of the surfactants in the liquid cleansing composition may be from about 5.0 wt %, about 6.0 wt %, about 7.0 wt %, about 8.0 wt % or about 9.0 wt % to about 10.0 wt %, about 11.0 wt %, about 12.0 wt %, about 13.0 wt %, or about 14.0 wt %. In another embodiment, the amount of the surfactants in the liquid cleansing composition may be from about 8.0 wt %/o to about 15.0 wt %. For example, the amount of the surfactants in the liquid cleansing composition may be from about 8.0 wt %, about 9.0 wt %, about 10.0 wt %, or about 11.0 wt %/o to about 12.0 wt %, about 13.0 wt %, about 14.0 wt %, or about 15.0 wt %. In another example, the amount of the surfactants in the liquid cleansing composition may be about 8.0 wt % to about 15.0 wt %, about 9.0 wt % to about 14.0 wt %, about 10.0 wt % to about 13.0 wt %, or about 11.0 wt % to about 12.0 wt %.

The salt of the $C_{10-16}$ alcohol ethoxylate sulfate may be any one or more salts of the $C_{10-16}$ alcohol ethoxylate sulfate. In at least one example, the $C_{10-16}$ may be lauryl. The average moles of ethylene oxide may be from 1 to 30. In a preferred embodiment, the average moles of the ethylene oxide is 1 to 3. The cation of the salt may be any suitable cation of the $C_{10-16}$ alcohol ethoxylate sulfate. For example, the cation may be an alkali metal (e.g., sodium, potassium, etc.), an alkaline earth metal (e.g., calcium), ammonium, triethanolamine, and the like. In an exemplary embodiment, the salt of the $C_{10-16}$ alcohol ethoxylate sulfate is sodium lauryl ether sulfate. The sodium lauryl ether sulfate may have an average of 2 moles of the ethylene oxide.

As previously discussed, the one or more surfactants may include a betaine surfactant. Illustrative betaine surfactants may include, but are not limited to, cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, and lauryl-bis-(2-hydroxypropyl)-carboxyethyl betaine, and the like, and combinations thereof. In a preferred embodiment, the betaine surfactant is a cocamidopropyl betaine. The alkyl polyglucoside may include any suitable alkyl group. For example, the alkyl group may be a decyl, a lauryl, or a coco. In a preferred embodiment, the alkyl polyglucoside is decyl glucoside.

In an exemplary embodiment, the surfactants of the liquid cleansing composition may include 60-70 weight % of the salt of a $C_{10-16}$ alcohol ethoxylate sulfate, 20-30 wt % betaine surfactant, and 5-15 wt % alkyl polyglucoside, based on a total weight of the surfactants. In another embodiment, the surfactants of the liquid cleansing composition may include 66 to 67 wt %, or about 66.4 wt % of the salt of a $C_{10-16}$ alcohol ethoxylate sulfate, 24 to 25 wt %, or about 24.4 wt % of the betaine surfactant, and 9 to 10 wt %, or about 9.2 wt % of the alkyl polyglucoside.

The compositions of the present disclosure include health care products such as skin care products, underarm products and hair care products, and include both rinse off compositions and leave-on compositions. Rinse off products include but are not limited to bar soap, body wash, shower gel, shampoo, conditioner, liquid hand or other soap, dish soap and facial wash; and leave on compositions include lotions, including but not limited to hand lotion and body lotion, creams including but not limited to facial cream, diaper cream and sunscreen cream, and underarm products including but not limited to antiperspirant sticks, gels, roll-on and pump sprays.

In some embodiments, the compositions of the present do not include dihydroquercetin or a derivative thereof. In some such embodiments, the compositions are hair care compositions. In some embodiments, the compositions do not contain any free (i.e., not incorporated into protein) amino acids other than taurine, arginine and glycine.

The compositions of the present disclosure can comprise a carrier. Suitable carriers for use with the compositions of the invention are well known in the art. The carrier can be a liquid, semi-solid or solid. Carriers among those useful herein include liquids, pastes, ointments, and gels, and can be transparent, translucent or opaque. The carrier may comprise any of a variety of materials, including emulsifiers, thickeners, fillers, and preservatives.

In at least one embodiment, the liquid cleansing composition may include at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, the anionic surfactant may be or include sodium lauryl sulfate. The anionic surfactants may also include higher alkyl-ether sulfates. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary embodiment, the anionic surfactant may be or include a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one embodiment, the liquid cleansing composition may include at least one nonionic surfactant. The nonionic surfactant may function as an emulsifier. Illustrative nonionic surfactants may include, but are not limited to, poloxamers and the like. For example, the nonionic surfactants may include polysorbate 20, poloxamer 407, poloxamer 338, poloxamer 124, and the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred embodiment, the nonionic surfactant is PEG 40 hydrogenated castor oil, which is commercially available as CREMOPHOR® RH40 from BASF Corp. of Florham Park, N.J.

The liquid cleansing composition may include one or more fatty alcohols. The fatty alcohols may be or include a $C_{12-18}$ fatty alcohol, or preferably a $C_{16-18}$ fatty alcohol. Illustrative fatty alcohols may include, but are not limited to, lauryl alcohol, myristyl alcohol, cetyl alcohol and stearyl alcohol. The amount of the fatty alcohols in the liquid cleansing composition may be greater than or equal to 8 wt % and less than or equal to 25 wt %.

The carrier of the liquid cleansing composition may be or include water. Water of the liquid cleansing composition may be deionized water, demineralized water, and/or softened water. In an exemplary embodiment, the carrier of the liquid cleansing composition includes demineralized water and softened water. Water may make up the balance of the liquid cleansing composition. For example, the amount of water in the liquid cleansing composition may be from about 10 wt % to 90 wt %, about 40 wt % to about 85 wt %, or about 60 wt % to about 80 wt %. In another example, the amount of water in the liquid cleansing composition may be at least 60 wt %, at least 65 wt %, at least 70 wt %, at least 72 wt %, at least 74 wt %, at least 76 wt %, at least 78 wt %, or at least 79 wt %. In at least one embodiment, the amount of demineralized water may be about 50 wt %, about 51 wt %, about 52 wt %, about 53 wt %, about 54 wt %, or about 55 wt %, and the amount of softened water may be about 18 wt %, about 19 wt %, about 20 wt %, about 21 wt %, or about 22 wt %. The amount of water in the liquid cleansing composition may include free water added and water introduced with other components or materials of the liquid cleansing composition. For example, the amount of the water in the liquid cleansing composition may include free water and water associated with the surfactants or any other component of the liquid cleansing composition.

In some embodiment, the liquid cleansing composition may include one or more skin care agents. Any suitable skin care agents that do not adversely affect the stability and/or efficacy of the liquid cleansing composition may be used. In at least one embodiment, the skin care agent may include an emollient configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., polyvinylpyrrolidine), protein derivatives (e.g., derivatized hydrolyzed wheat protein), ethoxylated fatty ethers, cellulosics (e.g., hydroxyethylcellulose), and the like, and combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred embodiment, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, and the like, and combinations thereof. In a preferred embodiment, the skin care agent is or includes a conditioner, such as a cationic cellulose polymer (e.g., polyquaternium-7).

The liquid cleansing composition may include one or more additional optional ingredients. Illustrative optional ingredients may include, but are not limited to, one or more dyes, fragrances, buffers and buffering agents (e.g., inorganic phosphates, sulfates, and carbonates), pH adjusters (e.g., acids and/or bases), preservatives (e.g., parabens, sodium salicylate, sodium benzoate, etc.), thickeners, viscosity modifiers, antioxidants, foam enhancers, chelating agents (e.g., EDTA, phosphates, etc.), opacifiers, hydric solvents, hydrotropes, humectants, antimicrobials, and the like, and combinations thereof.

In an embodiment, the compositions of the present disclosure further comprise a carrier comprising a personal care ingredient. The personal care ingredient is selected from, for example, a fragrance, a preservative, a solvent, a propellant, a skin cell renewal agent, an anti-acne drug, an antiperspirant compound, an insect repellent agent, a sunscreen agent, a decomposition product of an oil or a fat, an exfoliant, a surfactant, a soap and a mixture of two or more thereof.

Illustrative basic pH adjusters may include ammonia; mono-, di-, and tri-alkyl amines; mono-, di-, and tri-alkanolamines; alkali metal and alkaline earth metal hydroxides; and the like, and combinations thereof. For example, the basic pH adjuster may be ammonia, sodium hydroxide, potassium hydroxide, lithium hydroxide, monoethanolamine, triethylamine, isopropanolamine, diethanolamine, triethanolamine, and the like, and combinations thereof.

Illustrative acidic pH adjusters may include mineral acids and polycarboxylic acids. The mineral acids may be or include hydrochloric acid, nitric acid, phosphoric acid, sulfuric acid, and the like, and combinations thereof. The polycarboxylic acids may be or include citric acid, glycolic acid, lactic acid, and the like, and combinations thereof.

The liquid cleansing composition may have a neutral pH, an alkaline pH, or an acidic pH. In a preferred embodiment, the liquid cleansing composition is at least partially acidic. For example, the liquid cleansing composition may have a pH less than 7. In another example, the liquid cleansing composition may have a pH greater than or equal to 1 and less than 7. For example, the liquid cleansing composition may have a pH of about 1, about 2, about 3, or about 4 to about 5, about 6, or about 6.9. In another example, the liquid cleansing composition may have a pH from about 1 to less than 7, about 2 to about 6, or about 3 to about 5. In a preferred embodiment, the liquid cleansing composition has a pH from about 3.6 to about 4.2.

The foam enhancer may be or include, but is not limited to, cocamide MEA (i.e., cocamide monoethanolamide), cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and the like, and combinations thereof. In a preferred embodiment, the foam enhancer is cocamide MEA.

Illustrative humectants may include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and the like, and combinations thereof.

Another embodiment of the present disclosure is directed to a bar soap composition made from ingredients comprising: at least one cleanser chosen from soap and a first surfactant (sometimes referred to herein as a cleanser surfactant); and at least one taurate surfactant chosen from a salt of a fatty acid amide of taurine, a salt of a fatty acid amide of N-methyl taurine, and combinations thereof, the taurate surfactant being different than the first surfactant. The composition is in a solid bar form.

In an embodiment, the at least one cleanser employed in the bar soap is a soap. The term "soap" is defined herein as a salt of a fatty acid. In an embodiment, the soap is a salt of a $C_8$-$C_{22}$ carboxylic acid. For example, the salt can comprise at least one compound chosen from an alkali metal, such as sodium, or alkylammonium salt of a $C_8$-$C_{22}$ carboxylic acid, such as about a $C_{12}$-$C_{18}$ carboxylic acid. The amount of soap can range from about 60 weight % to about 95 weight %, such as about 70 weight % to about 80 weight %, based on the total weight of the final bar soap composition.

The fatty acid soap may comprise a neutralized fatty acid. Typical fatty acids used for soaps include myristic acid, lauric acid, palmitic acid, and stearic acids, as examples Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils.

The fatty acids may be neutralized with any base to form a soap. Typical bases include, but are not limited to, sodium hydroxide, potassium hydroxide, and triethanolamine. In certain embodiments, the fatty acid soap is formed from fatty acids neutralized by two or more bases. For example, sodium soaps, ammonium soaps, potassium soaps, magnesium soaps and calcium soaps can each be used alone as the soap ingredient, or as mixtures of two or more of the sodium, ammonium, potassium, magnesium and calcium soaps.

The soap can be made either in situ in amalgamate by mixing a source of fatty acids with the neutralizing agent, or the soap may be provided in a pre-made form. In certain embodiments, the molar amount of fatty acids is greater than the molar amount of neutralizing agent such that fatty acid remains in the amalgamate/pre-made soap. In some embodiments, the fatty acid soap is provided in the composition in the form of soap chips, as is known in the art.

The cleanser surfactant can be any surfactant suitable for use in bar soap. Examples of suitable surfactants can include PEG-12 and other PEGs, Polysorbate 20 and other polysorbates, synthetic detergents (e.g., Sodium Lauroyl Isethionate, sodium isethionate, etc.), Sodium tallowate, Cocamidopropyl betaine and Sodium salts of vegetable oils.

Any of the taurate surfactants disclosed herein, or combinations thereof, can be employed in the bar soap compositions of the present disclosure. The taurate surfactants can be in any suitable concentrations so long as the taurate surfactants remain stable in the bar soap formulation. Examples of suitable taurate surfactant concentrations range from about 0.1% to about 10% by weight of the final bar soap composition, such as about 0.1% to about 5% by weight of the composition, or about 1% to about 3% by weight of the composition. In an embodiment, the taurate surfactant, such as those of formula 1, are the only surfactants employed in the compositions of the present disclosure (e.g., where soap, rather than the first surfactant, is used as the cleanser), thereby providing one or more of the benefits described herein while potentially also acting as a surfactant.

Other ingredients can also be added to the bar soap. Examples of such ingredients include structuring agents, skin conditioning agents, chelating agents, foam boosters, preservatives, antimicrobial agents, exfoliating/scrubbing particles, glycerine, sodium chloride, titanium dioxide, colorants, fragrances and water. In an embodiment, the bar soap comprises at least one of glycerine and sodium chloride.

Suitable structuring agents (which may sometimes be referred to herein as structurants) include, for example, gellants selected from the group consisting of dibenzylidene sorbitol, dibenzylidene xylitol, dibenzylidene ribitol, and mixtures thereof. Other examples of structurants include alkali halides and alkali metal sulfates such as sodium chloride and sodium sulfate. Structurants may be incorporated into the compositions in an amount of up to 2 weight %, such as 0.1 to 1.5 weight % or 0.2 to 1 weight %, relative to the total weight of the final bar soap composition.

Skin conditioning ingredients (including emollients) that may be included in the bar soap compositions include: various fats and oils (for example, soybean oil, sunflower oil, canola oil, and shea butter; glyceryl esters (for example, PEG 6 caprylic/capric triglycerides, PEG 80 glyceryl cocoate, PEG 40 glyceryl cocoate, PEG 35 soy glyceride); alkyloxylated derivatives of dimethicone (for example, such as PEG/PPG-22/24 Dimethicone and PEG-8 Dimethicone); silicone esters (for example, Dimethicone PEG-7 isostearate); silicone quaternium compounds (for example, Silicone Quaternium-8); lanolin quaternium compounds (For example, quaternium-33); cationic polymers (for example, Polyquaternium-6 and Polyquaternium-7); and silicone polymers (for example, dimethiconol, dimethicone copolyol, alkyl dimethicone copolyol, and dimethicone copolyol amine.

Examples of foam boosters that may be incorporated into the bar soaps include certain amphoteric surfactants, cocomonoethanolamide (CMEA), cocoamidopropylamine oxide, cetyl dimethylamine chloride, decylamine oxide, lauryl/myristyl amidopropyl amine oxide, lauramine oxide, alkyldimethyl amine n-oxide, and myristamine oxide, in certain embodiments, the amount of foam booster is 2 weight % to 10 wt. % of the final bar soap composition.

A chelating agent may also be added to the to help retard oxidation. Any suitable chelating agent can be employed. For example, Ethylenediaminetetraacetic acid (EDTA) and salts thereof can be used as the chelating agent. The chelating agent is preferably present in amounts of about 0.01 wt. % to about 0.2 weight %, or about 0.025 weight % to about 0.1 weight % by total weight of the final bar soap composition, on an active basis.

The compositions of the present disclosure may also contain a preservative and/or antimicrobial agent in an amount of up to 1 weight %, or from about 0.01 wt. % to about 0.5 weight %, of the final bar soap composition on an active basis. Examples of preservatives include, but are not limited to, sorbic acid, potassium sorbate, methyl paraben, propyl paraben, imidazolinylurea, methylchloroisothiazolinone, and hydantoins (for example, DMDM hydantoin). Antimicrobial agents include, for example, triclocarban, triclosan and the like.

Particulate matter that aids exfoliation may further be incorporated into the bar soap. Particular matter includes polyethylene beads, jojoba beads, lufa, and oat flour.

Fragrance can be incorporated into the bar soap compositions in an amount of about 0.001 to about 2 wt. % of the final bar soap composition. The fragrance can include any active agent such as a phenolic, aldehyde, alcohol, nitrile, ether, ketone or ester and the like.

Water may be present in the bar soap in an amount of up to about 20 weight %, up to 15 weight %, or up to 10 weight % by total weight of the final bar soap composition. Preferably, water is present in an amount of from 5 weight % to 20 weight %, or from 8 weight % to 20 weight % or from 8 to 15 weight % of the final bar soap composition. The water can be added separately or made available from water contained in the other ingredients.

The pH of the bar soap composition can range, for example, from about 8.5 to about 12, such as about 9 to about 11, or about 9 to about 10. The pH test method is based on 1 g of bar soap dissolved into 99 g of water to make a 1 weight % soap solution, which is then tested for pH level.

In an embodiment, the final bar soap composition does not include a medically effective amount of antimicrobial agents, such as triclocarban or salicylic acid, for topical applications. The term "not a medically effective amount" as used herein is defined to mean less than 0.01% by weight. In an embodiment, the final bar soap composition includes less than 0.001% or less than 0.00001% of antimicrobial agents, such as triclocarban or salicylic acid, by weight, relative to the total weight of the final bar soap composition.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Synthesis Method 1

Direct reaction of ZnO and usnic acid. To a scintillation vial was added 21.2 mg of ZnO and 183.2 mg of usnic acid (2.04 eq.) followed by 4 mL of anhydrous EtOH. The capped mixture was stirred on a magnetic stirrer at ~80° C. overnight. Sample was dry on next day morning, having a bright red-purple color. Mass Spectra of the material dissolved in EtOH confirmed $Zn(Usn)_2$. However, the red color was impurity. A purification attempt was performed by dissolving a portion of the crude product in EtOH, filtering and precipitating the product with DI water. The precipitate formed a colloidal solution that could not be filtered. Estimated yield <50%.

Example 2—Synthesis Method 2

Synthesis from zinc acetate and sodium usnate. To a small 4 mL vial was added 31.9 mg of ZnO and 47.4 mg of acetic acid (2.01 eq.) followed by 0.5 mL of DI water. The solution was sonicated briefly to accelerate dissolution of ZnO to form a solution of zinc acetate ($ZnAc_2$). In a separate 20 mL scintillation vial, 271.2 mg (2.0 eq.) of usnic acid was added and stirred with a stirring bar. In third vial was mixed 63 mg of 50% NaOH (2.0 eq.) with 3 mL of anhydrous EtOH. The NaOH was then added into the vial with usnic acid and stirred briefly to obtain cloudy solution. Used 1 mL of EtOH to rinse the NaOH vial to transfer all into the usnic acid vial. The $ZnAc_2$ was slowly added to the sodium usnate while stirring. The mixture was stirred overnight at room temperature (although the reaction was perhaps completed in 1-2 hours). The crude mixture was filtered to remove undissolved residue and product precipitated from filtrate by dilution with water. After filtration and air-drying, the product $Zn(Usn)_2$ was obtained as a light yellow powder, estimated yield 80-92%. Analytical: Soluble in EtOH, insoluble in water. $^1H$ NMR (d6-DMSO, $\delta$): 1.57 ($CH_3$), 1.93 ($CH_3$), 2.41 ($CH_3$), 2.56 ($CH_3$), 5.71 (CH), 12.35 (OH), 13.32 (OH). IR (neat, $cm^{-1}$): 1696, 1626, 1552, 1389, 1371, 1284, 1190, 1143, 1118, 1065, 1037, 843. Elemental analysis: 7.87% Zn.

The $^1H$ NMR analysis of the purified complex showed that only 2 OH groups per usnic moiety are present in the complex, while there were 3 OH groups in usnic acid. NMR diffusion coefficient experiment suggests ratio of 2.5 between usnic acid and zinc. The IR analysis shows a shift of the carbonyl frequency in agreement with a metal binding. Elemental analysis of zinc is within 10% error, which further confirms the stoichiometry of 1:2 identified by NMR.

Example 3—Synthesis Method 3

Direct synthesis from zinc acetate and usnic acid. In a 20 mL scintillation vial was mixed 43.6 mg of ZnO, 279.5 mg of usnic acid (1.515 eq.) and 5 mL of anhydrous EtOH. While stirring, was added 61.4 mg of acetic acid (2.01 eq. to ZnO) and then continued to stir the solution at room temperature. After 2 hours, the residue was filtered out and the product was crashed from filtrate by taking it into water. The product was filtered, washed and dried to obtain 277.2 mg of a light yellow powder (91%).

Example 4—Solubility Determination

Solubility of Zn:usnate complex was performed using standard techniques. Solubility of usnic acid in DI water at 35° C. was reported to be 6.3 ppm (see Jin et al., Solubility of (+)-Usnic Acid in Water, Ethanol, Acetone, Ethyl Acetate and n-Hexane, *J Solution Chem.*, 2013, 42:1018-1027). Zn:usnate complex showed a solubility of 13.5 ppm in DI water at room temperature.

Example 5—In Vitro Cup Scrub AB Test of Soap Bars

Figure 4:
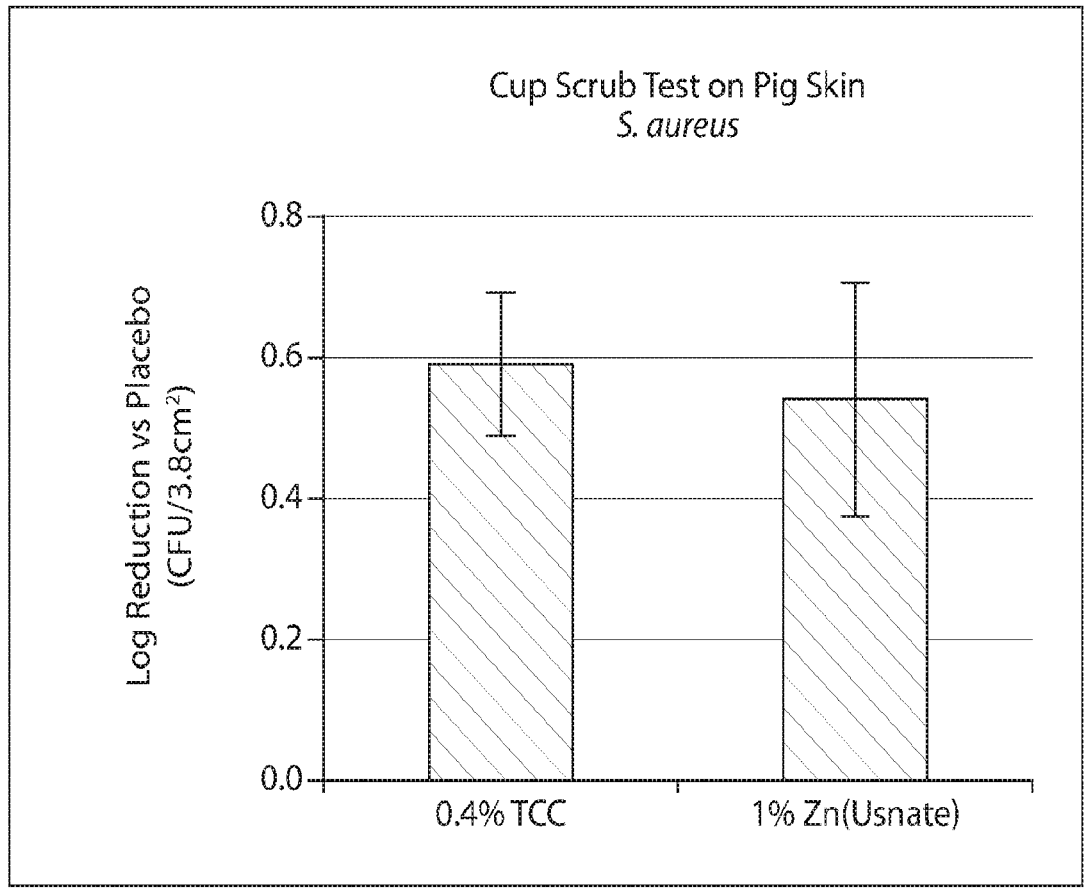
FIG. 4 is a graph depicting the reduction of residual bacterial counts versus placebo for soap noodles having either 0.4% TCC or 1% Zn:usnate complex.

This assay measures residual antibacterial efficacy. 1% Zn:usnate complex was added to base soap chips and processed into soap noodles. The noodle sample was wetted and rubbed against the porcine skin. The skin was then rinsed, lightly dried and inoculated with *S. aureus*. After incubation, bacteria recovered were harvested using a cup scrub technique and enumerated using standard plate count procedures. The mean log counts for colony forming units (CFU) were calculated for the duplicates. As a placebo, the base soap chips were processed into noodles. As a positive control, a soap formulation having sodium palmitate, sodium oleate, sodium laureth (sodium soap), water, glycerin, talc, PEG-12, fragrance, sodium chloride, triclocarban, citric acid, titanium dioxide, pentasodium pentetate, etidronic acid, yellow 10, orange 4 and further containing 0.4% triclocarban (TCC) was also processed into noodles. The comparison of the residual bacterial counts for these samples is shown in Table 1. The reduction of the residual bacterial count versus placebo were calculated and shown in FIG. 4. The data show 1% Zn:usnate complex performs at parity to 0.4% TCC.

TABLE 1

Results of cup scrub test on porcine skin.

| | | log *S. aureus* count (CFU/3.8 $cm^2$) | |
| --- | --- | --- | --- |
| run # | samples | avg (N = 2) | stdev (N = 2) |
| 1 | Placebo | 5.48 | 0.09 |
| | 0.4% TCC | 4.93 | 0.03 |
| | 1% Zn(Usnate) | 5.02 | 0.08 |
| 2 | Placebo | 5.50 | 0.02 |
| | 0.4% TCC | 4.88 | 0.03 |
| | 1% Zn(Usnate) | 4.88 | 0.11 |

Example 6—Minimal Inhibitory Concentration Determination

Minimal inhibition concentration (MIC) is the lowest concentration of an antimicrobial agent that can inhibit the visible growth of a microorganism after overnight incubation. The MIC values of zinc:usnate complex and usnic acid against *Staphylococcus aureus* and *Escherichia coli* were determined with the broth micro dilution method. Briefly, 0.1% stock solutions were prepared in dimethyl sulfoxide (DMSO). Using a 96-well microtitre plate, the corresponding testing concentrations are 500, 250, 125, 62, 31, 16, 8, 4, 2, 1, 0.5 and 0.2 ppm, respectively. The optic density readings at 610 nm for each well were used to assess the level of bacterial growth. The MIC results are listed in Table 2.

TABLE 2

Results of MIC Assay

| | MIC (ppm) | |
| --- | --- | --- |
| Samples | S. aureus (G+) | E. Coli (G−) |
| Usnic Acid | 4 | >125 |
| Zn:Usnate | 8 | >125 |

While the present invention has been described with reference to embodiments, it will be understood by those skilled in the art that various modifications and variations may be made therein without departing from the scope of the present invention.

What is claimed is:

1. A personal care composition comprising a Zn:usnate complex having a 1:2 zinc to usnate molar ratio;
   wherein the personal care composition has a pH from about 8.5 to about 12.

2. The personal care composition of claim 1, wherein said Zn:usnate complex has a solubility of about 13.5 ppm in water at room temperature.

3. The personal care composition of claim 2, wherein said complex has a minimal inhibitory concentration of about 8 parts per million against S. aureus.

4. The personal care composition according to claim 1, wherein the personal care composition is a rinse off composition selected from the group consisting of a body wash, a shower gel, a shampoo, a conditioner, a liquid hand or other soap, a dish soap and a facial wash.

5. The personal care composition according to claim 1, wherein the personal care composition is a leave-on composition selected from the group consisting of a lotion, a cream, an antiperspirant stick, a gel, and an aerosol.

6. The personal care composition of claim 4, wherein said composition comprises a cleansing component.

7. The personal care composition according to claim 6, wherein the cleansing component is a liquid soap or a liquid hand soap.

8. The personal care composition according to claim 6, wherein the cleansing component comprises one or more surfactants.

9. The personal care composition according to claim 8, wherein the cleansing component comprises at least 8.0 wt % of the one or more surfactants, or at least 9.0 wt % of the one or more surfactants.

10. The personal care composition according to claim 8, wherein the one or more surfactants comprise a betaine surfactant.

11. The personal care composition of claim 10, wherein the betaine surfactant is cocoamidopropyl betaine.

12. The personal care composition according to claim 8, further comprising a foam enhancer, wherein the foam enhancer is cocamide monoethanolamide.

13. A method of treating and/or preventing progression of microorganism induced ailments comprising applying an effective amount of a composition described in claim 1.

14. A method for cleaning teeth, reducing bacterially-generated biofilm and plaque, reducing gingivitis, and/or inhibiting tooth decay and formation of cavities comprising applying an effective amount of the composition of claim 1 to a tooth surface.

15. A method for controlling microbial growth on a skin surface comprising applying an effective amount of the composition of claim 1 to a skin surface.

16. A method of making the personal care composition of claim 1, comprising combining usnic acid or usnate and a zinc source in a liquid medium, isolating the complex thus formed in solid form, and combining the zinc:usnate complex with a personal care composition.

17. A personal care composition comprising:
   a Zn:usnate complex having a 1:2 zinc to usnate molar ratio,
   wherein the personal care composition is a bar soap.

18. The personal care composition of claim 17, comprising:
   at least one cleanser selected from soap and a first surfactant; and
   at least one taurate surfactant selected from a salt of a fatty acid amide of taurine, a salt of a fatty acid amide of N-methyl taurine, and combinations thereof, wherein the taurate surfactant is different from the first surfactant.

* * * * *